United States Patent

Kaihoh et al.

[11] Patent Number: 6,060,485
[45] Date of Patent: May 9, 2000

[54] ARYLACETIC AMIDE DERIVATIVE OR SALT THEREOF, AND PHARMACEUTICAL COMPRISING IT

[75] Inventors: Terumitsu Kaihoh; Tomomi Okada, both of Narita; Yoshinori Takahashi, Chiba; Hiroyuki Mizuno, Chiba; Haruyoshi Honda, Chiba; Susumu Sato, Narita, all of Japan

[73] Assignee: SSP Co., Ltd., Tokyo, Japan

[21] Appl. No.: 09/181,091

[22] Filed: Oct. 28, 1998

[30] Foreign Application Priority Data

Oct. 31, 1997 [JP] Japan .................................. 9-300352

[51] Int. Cl.[7] .................... A61K 31/445; C07D 211/58; C07D 401/12
[52] U.S. Cl. ................. 514/318; 514/235.5; 514/326; 544/129; 546/193; 546/222; 546/224
[58] Field of Search ................... 546/193, 222, 546/224; 544/129; 514/318, 326, 235.5

[56] References Cited

U.S. PATENT DOCUMENTS

| | | | |
|---|---|---|---|
| 2,816,895 | 12/1957 | Ehrhart et al. | 546/222 |
| 4,405,627 | 9/1983 | Masi | 514/352 |
| 4,584,303 | 4/1986 | Huang | 514/326 |
| 5,066,680 | 11/1991 | Shiokawa | 514/622 |
| 5,750,540 | 5/1998 | Tsuchiya | 514/318 |

FOREIGN PATENT DOCUMENTS

| | | |
|---|---|---|
| 0 383 256 | 8/1990 | European Pat. Off. . |
| 0 751 127 | 1/1997 | European Pat. Off. . |
| 0 823 423 | 2/1998 | European Pat. Off. . |
| 0 863 141 | 9/1998 | European Pat. Off. . |
| 93/16048 | 8/1993 | WIPO . |
| WO 96/33973 | 10/1996 | WIPO . |
| WO 97/13766 | 4/1997 | WIPO . |

OTHER PUBLICATIONS

Riotte et al. "Studies of the spasmolytic activity of . . . " CA 106:207197, 1987.

Okada et al. "Preparation of N–piperidinyl . . . " CA 126:144121, 1997.

Taniguchi et al. "Agents for the treatment of overactive . . . " CA 122:81073, 1994.

Patent Abstracts of Japan, vol. 097, No. 003, Mar. 31, 1997, JP 08 291141, Nov. 5, 1996.

Chemical Abstracts, vol. 118, No. 23, Jun. 7, 1993, AN 231037, J.M. Wilkes, et al., "Second Messengers in the Gastric Gland: A Focus on Calcium", 1991.

Chemical Abstracts, vol. 115, No. 11, Sep. 16, 1991, AN 106867, A. Leonard, et al., "M3–Subtype Muscarinic Receptor That Controls Intracellular Calcium Release and Inositol Phosphate Accumulation in Gastric Parietal Cells", 1991.

Chemical Abstracts, vol. 122, No. 17, Apr. 24, 1995, AN 205037, M. Toselli, et al., "Muscarine Inhibits High–Threshold Calcium Currents with Two Distinct Modes in Rat Embryonic Hyppocampal Neurons", 1995.

*Primary Examiner*—Ceila Chang
*Attorney, Agent, or Firm*—Oblon, Spivak, McClelland, Maier & Neustadt, P.C.

[57] ABSTRACT

Described is an arylacetic amide derivative represented by the following formula (1):

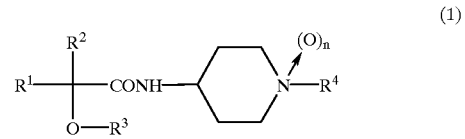

wherein $R^1$ represents an aryl group or the like, $R^2$ and $R^3$ each independently represents an alkyl group, a cycloalkyl group or the like, and $R^4$ represents an aralkyl group, an alkyl group or the like; or salt thereof. The compound according to the present invention has both excellent anticholinergic action and calcium antagonism and at the same time has high selectivity to bladder, so that it is useful as a preventive or remedy for urinary disorders.

5 Claims, No Drawings

ARYLACETIC AMIDE DERIVATIVE OR SALT THEREOF, AND PHARMACEUTICAL COMPRISING IT

BACKGROUND OF THE INVENTION

1. Field of the Invention

This invention relates to a novel arylacetic amide derivative or salt thereof. More specifically, the present invention pertains to an arylacetic amide derivative or salt thereof which has both anticholinergic action and calcium antagonism and is useful as a pharmaceutical for the prevention or treatment of urinary disorders such as pollakiuria or urinary incontinence in the diseases caused by nervous pollakiuria, neurogenic bladder, nocturnal enuresis, unstable bladder or chronic cystitis.

2. Description of the Related Art

A medicament which inhibits reflex bladder contraction is useful for the prevention or treatment of urinary disorders such as pollakiuria or urinary incontinence in the diseases caused by nervous pollakiuria, neurogenic bladder, nocturnal enuresis, unstable bladder or chronic cystitis.

As a medicament which inhibits reflex bladder contraction, reported to date are oxybutynin hydrochloride, propiverine hydrochloride, vamicamide, tolterodine and compounds as described in Japanese Patent Application Laid-Open Nos. HEI 2-262548, 6-92921, 6-135958, 7-258250, 8-291141 and 9-71563 and W093/16048, W095/06635, WO96/33973, WO97/13766 and W097/45414.

Each of the above-described compounds, however, does not have sufficient effects for inhibiting reflex bladder contraction or even if having sufficient effects, dry mouth (inhibitory action of salivation), which is a side effect due to the anticholinergic action, occurs even by the pharmaceutically effective amount of it. In other words, the main effect is not clearly separated from the side effect, which is regarded as a clinical problem.

SUMMARY OF THE INVENTION

An object of the present invention is therefore to provide a compound which inhibits reflex bladder contraction and has high safety with less incidence of dry mouth (inhibitory action of salivation) which is a side effect and is therefore useful as a pharmaceutical for the prevention or treatment of urinary disorders.

With the forgoing in view, the present inventors have synthesized various compounds and conducted extensive investigation on their action. As a result, it has been found that a novel arylacetic amide derivative represented by the below-described Formula (I) has excellent anticholinergic action and calcium antagonism and is safe with reduced side effects such as dry mouth so that it is useful for the prevention and treatment of urinary disorders, leading to the completion of the present invention.

In one aspect of the present invention, there is thus provided an arylacetic amide derivative represented by the following formula (1):

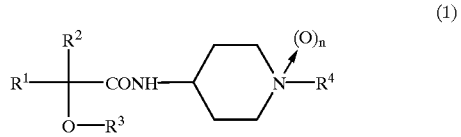

(1)

wherein $R^1$ represents a substituted or unsubstituted aromatic hydrocarbon or heteroaromatic group, $R^2$ and $R^3$ each independently represents a substituted or unsubstituted hydrocarbon or heterocyclic group, $R^4$ represents a hydrogen atom or a substituted or unsubstituted hydrocarbon or heterocyclic group and n stands for 0 or 1; or salt thereof.

In another aspect of the present invention, there is also provided a pharmaceutical which comprises as an effective ingredient said arylacetic amide derivative (1) or salt thereof.

In a further aspect of the present invention, there is also provided a pharmaceutical composition which comprises said arylacetic amide derivative (1) or salt thereof and a pharmaceutically acceptable carrier.

In a still further aspect of the present invention, there is also provided the use of said arylacetic amide derivative (1) or salt thereof as a pharmaceutical.

In a still further aspect of the present invention, there is also provided a method of treating urinary disorders, which comprises administering said arylacetic amide derivative (1) or salt thereof.

The arylacetic amide derivative or salt thereof according to the present invention has excellent anticholinergic action and calcium antagonism and has high selectivity for the bladder over the salivary gland so that it is useful as a preventive or remedy for various urinary disorders.

DETAILED DESCRIPTION OF THE PREFERRED EMBODIMENTS

In the formula (1) which represents the arylacetic amide derivative of the present invention, examples of the aromatic hydrocarbon group represented by $R^1$ include phenyl and naphthyl, of which the phenyl is particularly preferred. Examples of the heteroaromatic group include monocyclic groups and fused cyclic groups each containing nitrogen, oxygen and/or sulfur as a hetero atom. Specific examples include thienyl, furanyl, imidazolyl, pyridyl, pyrazyl, pyrimidyl, pyridazyl, quinolyl, isoquinolyl, quinazolyl, quinoxalyl and cinnolyl.

Examples of the group substitutable for the above-described aromatic hydrocarbon or heteroaromatic group include halogen, $C_{1-6}$ alkyl, halogeno($C_{1-6}$ alkyl), $C_{1-6}$ alkoxy, amino, benzyloxy, cyano, benzoyl, $C_{1-6}$ alkanoyl, carbamoyl, carboxy, carboxy($C_{1-6}$ alkyl), $C_{1-6}$ alkanoyloxy, nitro and sulfonamide. The number of these substituents preferably ranges from 1 to 5. Here, examples of the $C_{1-6}$ alkyl moiety of the $C_{1-6}$ alkyl, halogeno($C_{1-6}$ alkyl) or carboxy($C_{1-6}$ alkyl) group include methyl, ethyl, n-propyl, i-propyl, n-butyl, i-butyl, sec-butyl, t-butyl, n-pentyl, i-pentyl and n-hexyl. Examples of the $C_{1-6}$ alkanoyl moiety of the $C_{1-6}$ alkanoyl and $C_{1-6}$ alkanoyloxy group include formyl, acetyl, propionyl, n-butyryl, i-butyryl, n-valeryl, i-valeryl and pivalyl. Examples of the $C_{3-8}$ alkoxy group include methoxy, ethoxy and isopropoxy. Examples of the halogen atom include chlorine, bromine, fluorine and iodine.

Examples of the hydrocarbon group represented by $R^2$ or $R^3$ include saturated or unsaturated (including aromatic) hydrocarbon groups, of which the linear, branched or cyclic alkyl, alkenyl and aralkyl groups are preferred. These groups may each be substituted with a hydroxy, amino, substituted amino or heteroaromatic group. As the substituted or unsubstituted hydrocarbon group represented by $R^2$ or $R^3$, a $C_{1-8}$ linear, branched, cyclic or cyclic-linear alkyl, $C_{2-6}$ alkenyl group, phenyl($C_{1-6}$ alkyl) or heteroaromatic-($C_{1-6}$ alkyl) group which may be substituted with a hydroxy, amino or substituted amino group are more preferred. Examples of the $C_{1-8}$ linear or branched alkyl group which may be substituted with a hydroxy, amino or substituted amino group include methyl, ethyl, n-propyl, i-propyl, n-butyl, i-butyl, sec-butyl, t-butyl, n-pentyl, i-pentyl, n-hexyl, i-hexyl, n-heptyl, i-heptyl, n-octyl and i-octyl groups. As the cycloalkyl group which may be substituted with a hydroxy, amino or substituted amino group, $C_{2-8}$ cycloalkyl groups are preferred and examples include cyclopropyl, cyclobutyl, cyclopentyl, cyclohexyl, cycloheptyl and cyclooctyl. Examples of the $C_{3-8}$ alkenyl group include vinyl, allyl, isopropenyl, butenyl, pentenyl and hexenyl. Examples of the phenyl($C_{1-6}$ alkyl) group include benzyl, phenethyl and phenylpropyl. The heterocyclic and $C_{1-6}$ alkyl moieties of the heteroaromatic-$C_{1-6}$ alkyl group have the same meanings as those described in $R^1$.

In the substituent of $R^2$ or $R^3$, examples of the substituted amino group include alkylamino, dialkylamino, cyclic amino and aralkylamino groups and specific examples include methylamino, ethylamino, n-propylamino, i-propylamino, dimethylamino, diethylamino, dipropylamino, di-i-propylamino, pyrrolidino, piperidino, piperazino, morpholino, benzylamino and phenethylamino.

As the heterocyclic group represented by $R^2$ or $R^3$, the nitrogen-containing heterocyclic group is preferred and examples include pyrrolidinyl, piperidinyl and piperazinyl.

Examples of the hydrocarbon group represented by $R^4$ include saturated or unsaturated (including aromatic) hydrocarbon groups, more specifically, $C_{1-6}$ alkyl, $C_{2-6}$ alkenyl, phenyl, naphthyl and phenyl($C_{1-6}$ alkyl) groups.

The $C_{1-6}$ alkyl and $C_{2-6}$ alkenyl groups have the same meanings as described above. Examples of the heterocyclic group represented by $R^4$ include thienyl, furanyl, imidazolyl, pyridyl, pyrazyl, pyrimidyl, pyridazyl, quinolyl, isoquinolyl, quinazolyl, quinoxalyl and cinnolyl.

As the substituent for the above-described hydrocarbon or heterocyclic group, usable are 1 to 5 substituents selected from the group consisting of halogen, halogeno($C_{1-6}$ alkyl), $C_{1-6}$ alkyl, $C_{1-6}$ alkoxy, amino, benzyloxy, cyano, benzoyl, $C_{1-6}$ alkanoyl, carbamoyl, carboxy, carboxy($C_{1-6}$ alkyl) and $C_{1-6}$ alkanoyloxy, nitro and sulfonamide. These substituents have specifically the same meanings as described above in $R^1$. As the example of the substituted alkyl group, the above-described $C_{1-6}$ alkyl group substituted with a heteroaromatic group may be mentioned.

In the formula (1), preferred examples of $R^1$ include phenyl, naphthyl, thienyl, furanyl, imidazolyl, pyridyl, pyrazyl, pyrimidyl, pyridazyl, quinolyl, isoquinolyl, quinazolyl, quinoxalyl and cinnolyl groups which may each be substituted with 1 to 5 substituents selected from halogen, halogeno($C_{1-6}$ alkyl), $C_{1-6}$ alkyl, $C_{1-6}$ alkoxy, amino, benzyloxy, cyano, benzoyl, $C_{1-6}$ alkanoyl, carbamoyl, carboxy, carboxy($C_{1-6}$ alkyl), $C_{1-6}$ alkanoyloxy, nitro and sulfonamide. Preferred examples of $R^2$ or $R^3$ include $C_{1-8}$ linear, branched, cyclic or cyclic-linear alkyl, $C_{2-6}$ alkenyl, phenyl($C_{1-6}$ alkyl), nitrogen-containing saturated heterocyclic and heteroaromatic-($C_{1-6}$ alkyl) groups which may each be substituted with a hydroxy, amino or substituted amino group. Preferred examples of $R^4$ include a hydrogen atom; a $C_{1-6}$ alkyl group; and a phenyl, naphthyl, thienyl, furanyl, imidazolyl, pyridyl, pyrazyl, pyrimidyl, pyridazyl, quinolyl, isoquinolyl, quinazolyl, quinoxalyl, cinnolyl, phenyl ($C_{1-6}$ alkyl), $C_{2-6}$ alkenyl and heteroaromatic-($C_{1-6}$ alkyl) groups which may each be substituted with 1 to 5 substituents selected from the group consisting of halogen, halogeno ($C_{1-6}$ alkyl), $C_{1-6}$ alkyl, $C_{1-6}$ alkoxy, amino, benzyloxy, cyano, benzoyl, $C_{1-6}$ alkanoyl, carbamoyl, carboxy, carboxy ($C_{1-6}$ alkyl), $C_{1-6}$ alkanoyloxy, nitro and sulfonamide.

In the compound (1) according to the present invention, that having as $R^1$ an aryl group, particularly a phenyl group, is preferred. As $R^2$ or $R^3$, alkyl and cycloalkyl groups are preferred, with a $C_{1-6}$ alkyl group such as methyl, ethyl, n-propyl, i-propyl and n-butyl and a $C_{3-6}$ cycloalkyl group such as cyclopropyl, cyclobutyl, cyclopentyl and cyclohexyl being particularly preferred. As $R^4$, $C_{1-6}$ alkyl and aralkyl groups are preferred, with a benzyl group being particularly preferred.

There is no particular limitation imposed on the salt of the arylacetic amide derivative (1) of the present invention insofar as it is pharmaceutically acceptable. Examples include salts with an organic acid such as formate, acetate, trifluoroacetate, fumarate, maleate, tartrate, methanesulfonate, benzenesulfonate and p-toluenesulfonate; and salts with an inorganic acid such as hydrochloride, hydrobromide, hydroiodide, sulfate and phosphate. The arylacetic amide derivative (1) contains an asymmetric carbon so that there exist stereoisomers based on it. All the isomers are embraced in the present invention. The arylacetic amide derivative (1) may exist as a solvate typified by hydrate.

The arylacetic amide derivative (1) of the present invention can be prepared, for example, in accordance with any one of the following preparation processes 1 to 4.

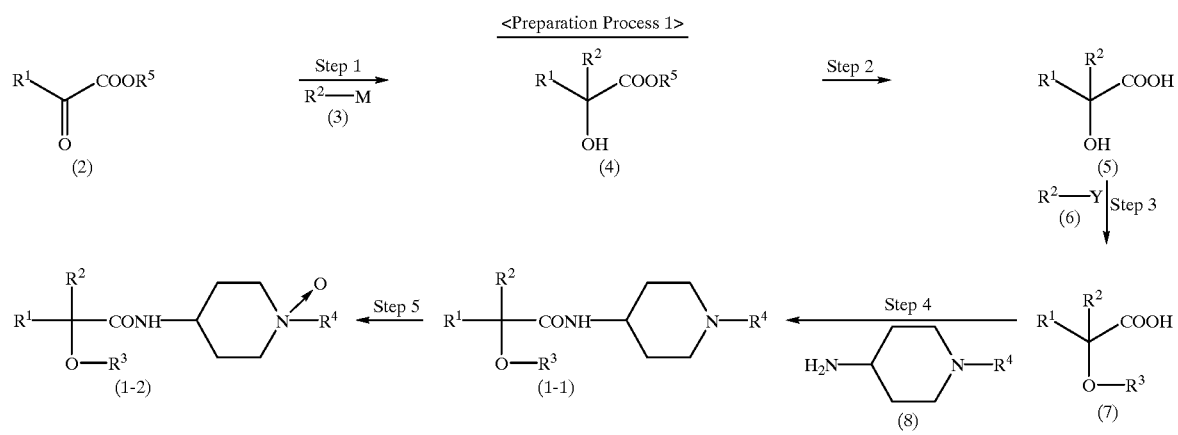

wherein $R^1$ to $R^4$ have the same meanings as described above, $R^5$ represents a lower alkyl group, M represents an alkali metal or MgX (in which X representing a halogen atom) and Y represents a halogen atom or a substituted sulfonyloxy group.

In the preparation process 1, an α-keto ester (2) is reacted with Compound (3) (step 1) and the resulting compound (4) is hydrolyzed, whereby the corresponding carboxylic acid derivative (5) is obtained (step 2). The hydroxy group of Compound (5) is alkylated with Compound (6) to obtain Compound (7) (step 3), followed by 10 condensation with Compound (8), whereby an invention compound (1-1) is obtained (step 4). By the oxidation of the invention compound (1-1), an invention compound (1-2) can be prepared (step 5). Each step will next be described more specifically.

[Step 1]

The α-keto ester (2), which is a starting material, is commercially available or can be prepared by a known method (for example, a process as described in Journal of Organic Chemistry, 46, 213(1981), Synthetic Communication, 11, 943(1981) or the like). Compound (3) can be prepared from $R^2$-X (X has the same meaning as described above) by a known method.

The reaction of the step 1 is usually carried out in the presence of a solvent. There is no particular limitation imposed on the solvent to be employed insofar as it does not take part in the reaction. Examples include diethyl ether, tetrahydrofuran and n-hexane. No particular limitation is imposed on the reaction temperature. The reaction may be effected at a temperature ranging from –20° C. to reflux under heating.

[Step 2]

Compound (4) can be converted into Compound (5) by the hydrolysis under basic conditions in a conventional manner Examples of the base to be employed include sodium hydroxide, potassium hydroxide and potassium t-butoxide. Examples of the reaction solvent include methanol-water, ethanol-water and dioxane-water mixed solvents. The reaction is desirably effected at a temperature ranging from room temperature to reflux temperature for about 1 to 12 hours.

[Step 3]

Compound (7) can be obtained by reacting Compound (5) with Compound (6). Suitable examples of the group Y in Compound (6) include fluorine, chlorine, bromine, iodine, mesyloxy and tosyloxy, of which iodine is most preferred. This reaction is effected in a suitable solvent in the presence of a base. A phase transfer catalyst is sometimes employed, which depends on the kind of Compound (6). Examples of the solvent to be employed in this reaction include dimethylformamide, dimethyl sulfoxide, methanol, ethanol, ethoxyethanol, tetrahydrofuran, dioxane and acetonitrile. Examples of the base include triethylamine, N,N-diisopropylethylamine, pyridine, sodium hydroxide, potassium hydroxide, potassium carbonate, sodium bicarbonate, sodium hydride and calcium hydride. The reaction is effected at a temperature ranging from room temperature to stirring under heat.

[Step 4]

The invention compound (1-1) can be obtained by converting Compound (7) to the corresponding acid chloride and then reacting the acid chloride with Compound (8) or by reacting Compound (7) with Compound (8) in the presence of a suitable condensing agent.

Examples of the reagent to be employed upon conversion of Compound (7) to the corresponding acid chloride include oxalyl chloride and thionyl chloride. Examples of the suitable condensing agent include carbonyldiimidazole, 1-hydroxy-2(1H)-pyridone, N-hydroxysuccinimide, diphenylphosphoryl azide, N,N-dicyclohexylcarbodiimide and 1-ethyl-3-(3-dimethylaminopropyl)-carbodiimide-hydrochloride. The reaction is sometimes effected in the presence of a suitable base, for example, an organic base such as triethylamine or pyridine, which depends on the kind of the condensing agent.

There is no particular limitation imposed on the solvent to be employed for the above reactions insofar as it does not take part in the reactions. Examples include benzene, toluene, diethyl ether, tetrahydrofuran, chloroform, dichloromethane and N,N-dimethylformamide.

[Step 5]

The invention compound (1-2) can be prepared by reacting the invention compound (1-1) in the presence of a suitable oxidizing agent. Examples of the oxidizing agent usable here include hydrogen peroxide-acetic acid, m-chloroperbenzoic acid, persuccinic anhydride and perbenzoic acid.

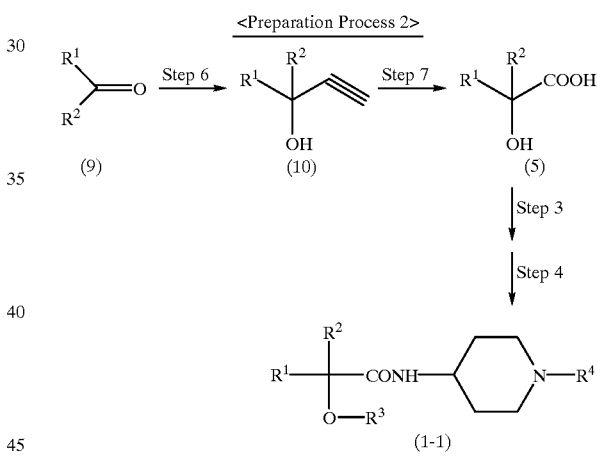

wherein $R^1$ to $R^4$ have the same meanings as described above.

In the preparation process 2, the compound represented by the formula (9) is reacted with lithium acetylide to obtain Compound (10) (step 6), followed by oxidation with an appropriate oxidizing agent, whereby Compound (5) is obtained (step 7). The resulting Compound (5) is treated as in the step 3 and step 4 of Preparation Process 1, whereby the invention compound (1-1) can be prepared. The step 6 and step 7 will next be described more specifically.

[Step 6]

In accordance with a known method (for example, the method as described in Journal of Organic Chemistry, 27, 240(1962)), a solution of the compound represented by the formula (9) in dimethyl sulfoxide is added to a solution of lithium acetylide-ethylenediamine complex in dimethyl sulfoxide, followed by stirring at room temperature for 2 to 12 hours, whereby the compound represented by the formula (10) can be prepared.

[Step 7]

In accordance with a known method (for example, the method as described in Journal of Organic Chemistry, 27, 240(1962)), an aqueous solution of potassium permanganate is added to the compound of the formula (10), followed by the reaction at room temperature for 1 to 6 hours, whereby the compound of the formula (5) can be prepared.

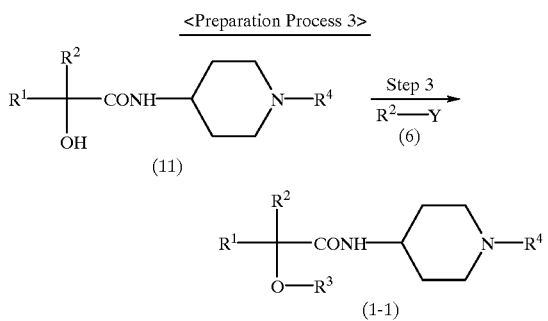

wherein $R^1$ to $R^4$ and Y have the same meanings as described above.

In the preparation process 3, the invention compound (1-1) can be prepared by treating the compound of the formula (11) in accordance with the step 3 of Preparation Process 1. Compound (11), which is a starting material, can be synthesized by the process as described in Japanese Patent Application Laid-Open No. Hei 9-71563.

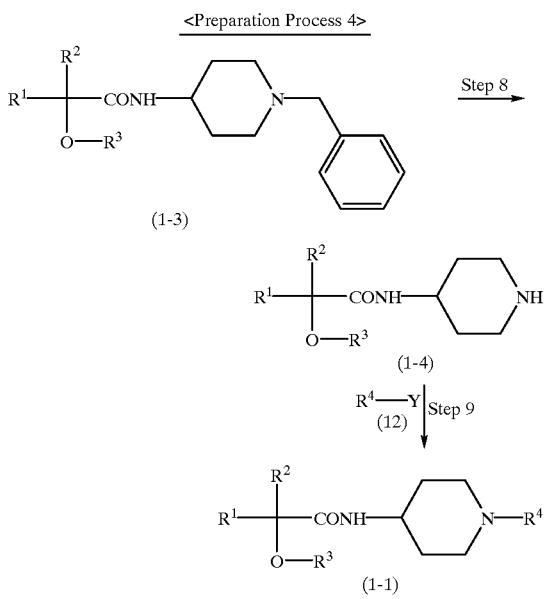

wherein $R^1$ to $R^4$ and Y have the same meanings as described above.

In Preparation Process 4, the invention compound (1-3) which is similar to the invention compound (1-1) except for having a benzyl group as $R^4$ is converted into the invention compound (1-4) by catalytic reduction (step 8), followed by the reaction with Compound (12), whereby the invention compound (1-1) can be prepared (step 9). Each step will next be descried more specifically.

<Step 8>

Examples of the catalyst to be used suitably for the catalytic reduction of the invention compound (1-3) include palladium catalysts such as palladium-carbon, palladium-black and palladium hydroxide-carbon, platinum catalysts such as platinum oxide and platinum black and nickel catalysts such as Raney nickel. The reaction is usually effected in the presence of a solvent. No particular limitation is imposed on the solvent insofar as it takes no part in the reaction. Examples include methanol, ethanol, dioxane and dimethylformamide. Although no particular limitation is imposed on the reaction temperature, the reaction may be carried out at a temperature ranging from room temperature to heating.

<Step 9>

The reaction of the invention compound (1-4) with Compound (12) is usually carried out in the presence of an appropriate base and solvent. Examples of the base to be employed include inorganic bases such as sodium hydroxide, potassium hydroxide, sodium carbonate and potassium carbonate and organic bases such as triethylamine and pyridine. There is no particular limitation imposed on the solvent to be employed in this step insofar as it is inert to the reaction. Examples include ethers such as ethyl ether, tetrahydrofuran and dioxane; mixed solvents such as dioxane-water, chlorinated hydrocarbons such as dichloromethane and chloroform, alcohols such as methanol and ethanol, and amides such as dimethylformamide, dimethylacetamide and N-methyl-α-pyrrolidone. Although no particular limitation is imposed on the reaction temperature, the reaction may be effected at a temperature ranging from room temperature to reflux under heating.

The isolation or purification of each of the target compounds in the above reactions can be conducted in a conventional manner, for example, washing, extraction, distillation, sublimation, recrystallization, chromatography on the like. Conversion into the corresponding salt or hydrate can also be conducted in a conventional manner.

The invention compound (1) has excellent anticholinergic action and calcium antagonism, inhibits reflex bladder contraction and has high safety with less incidence of dry mouth, which is a side effect of this compound, so that it is useful as a preventive or remedy for urinary disorders such as pollakiuria or urinary incontinence in the diseases caused by nervous pollakiuria, neurogenic bladder, nocturnal enuresis, unstable bladder or chronic cystitis.

When the invention compound is used as a pharmaceutical, it may be mixed with a pharmaceutically acceptable carrier and formulated into a pharmaceutical composition (pharmaceutical preparation) suited for parenteral administration, oral administration or external administration. Examples of pharmaceutical preparation include liquid preparations such as injections, inhalations, syrups and emulsions; solid preparations such as tablets and capsules; and external preparations such as ointments and suppositories. Such preparations may each contain an ordinarily employed additive such as adjuvant, stabilizer, humectant, emulsifier, absorption enhancer or surfactant as needed. Examples of the additive include distilled water for injection, Ringer's injection, glucose, sucrose syrup, gelatin, edible oil, cacao butter, magnesium stearate and talc.

Although the dosage of the invention compound (1) to be used as a preventive or remedy for urinary disorders varies depending on the administration route and age or weight of the patient, the compound is preferably administered to an adult at a daily dosage of 0.1 to 1000 mg in the case of oral administration. In addition to the administration to human, the invention compound (1) can also be used as a veterinary medicine for mammals.

EXAMPLES

The present invention will hereinafter be described more specifically by preparation examples, examples and tests, but it should however be borne in mind that they are only exemplary and the present invention is not limited to or by these examples.

Preparation Example 1

Preparation of ethyl 2-cyclohexyl-2-hydroxy-phenylacetate (Compound (4))

A solution of Grignard reagent prepared from cyclopentyl bromide (66 g) and magnesium (9 g) in absolute ether (240 ml) was added dropwise to a solution of ethyl phenylglyoxylate (30 g) in absolute ether (100 ml) at gently refluxing temperature. After the addition was completed, the reaction mixture was refluxed for 2 hours. The mixture was added to ice water (200 ml) and 10% diluted sulfuric acid (200 ml). The ether layer was separated from the reaction mixture, and then the aqueous layer was extracted with ether. The combined extracts were washed with water and dried over anhydrous sodium sulfate. The solvent was removed under pressure. The residue was vacuum distilled to obtain the title compound (23.5 g, 53.3%) as a pale yellow oil: bp 148 to 150° C. (6.5 mmHg).

$^1$H-NMR (CDCl$_3$)δ:1.08–2.24(11H,m), 1.28(3H,t), 3.73 (1H,brs), 4.17–4.28(2H,m), 7.24–7.35(3H,m), 7.63–7.66 (2H,m).

Preparation Example 2

Preparation of 2-cyclohexyl-2-hydroxy-phenylacetic acid (Compound (5))

A dissolved solution of ethyl 2-cyclohexyl-2-hydroxy-phenylacetate (Compound (4), 8.0 g) in methanol (150 ml) and 1N aqueous sodium hydroxide solution (60 ml) was refluxed for 3 hours and then, methanol was then removed under pressure. The residual solution was acidified with diluted hydrochloric acid, and extracted with ethyl acetate. The extract was washed with water, and dried over anhydrous sodium sulfate. The solvent was removed under pressure. The residue was recrystallized from hexane-ether to obtain the title compound (5.65 g, 80.3%) as a colorless crystal.

$^1$H-NMR (CDCl$_3$)δ:0.82–2.55 (11H,m), 5.82(2H,brs), 7.23–7.82(5H,m).

Preparation Example 3

Preparation of 2-ethoxy-3-methyl-2-phenylbutanoic acid (Compound (7))

To a solution of 2-hydroxy-3-methyl-2-phenylbutanoic acid (Compound (5), 30.0 g) in dimethyl sulfoxide (250 ml) was added 85% powdered potassium hydroxide (60 g) and the mixed solution was stirred for one hour. Under ice cooling, ethyl iodide (55 ml) was added and the resulting mixture was stirred at room temperature for 3 days. After the addition of water (100 ml), the resulting mixture was stirred at 80° C. for 6 hours. The reaction mixture was acidified with 1N hydrochloric acid, followed by extraction with ether. The ether layer was dried over anhydrous sodium sulfate and removed under reduced pressure. To the residue, hexane (200 ml) was added. After the resulting mixture was allowed to stand overnight, the crystals so precipitated were removed by filtration. The filtrate was removed under reduced pressure to obtain the title compound (27.0 g, 78.7%) as an oil.

$^1$H-NMR (CDCl$_3$)δ:0.63–1.40 (9H,m), 2.65(1H,q), 3.37 (2H,q), 7.24–7.82(5H,m).

Preparation Example 4

Preparation of 1-cyclobutyl-1-phenyl-2-propin-1-ol (Compound (10))

To s solution of lithium acetylido-ethylenediamine complex (8.46 g) in dimethyl sulfoxide (100 ml) was added a solution of cyclobutyl phenyl ketone (9.20 g) in dimethyl sulfoxide (30 ml), followed by stirring at room temperature for 4 hours. The reaction mixture was poured into ice water and then extracted with ether. The extract was washed with water and saturated saline and dried over anhydrous sodium sulfate. The solvent was then removed under reduced pressure. The residue was purified by a silica gel column (hexane:ethyl acetate=10:1) to obtain the title compound (5.80 g, 68.8%) as an yellow oil.

$^1$H-NMR (CDCl$_3$)δ:1.51–3.17 (7H,m), 2.71(1H,s), 7.23–7.72(5H,m).

Preparation Example 5

Preparation of 2-cyclobutyl-2-hydroxy-2-phenylacetic acid (Compound (5))

To 1-cyclobutyl-1-phenyl-2-propin-1-ol (Compound (10), 5.80 g), water (20 ml) was added. Under stirring, an aqueous solution (300 ml) of potassium permanganate (14.0 g) was added dropwise to the resulting mixture at 0° C., followed by vigorous stirring for further 2 hours. Sodium sulfite was added to the reaction mixture at room temperature. The precipitate so obtained was filtered through Celite and the filtrate was extracted with ether. The organic layer was dried over anhydrous sodium sulfate. The solvent was then removed under reduced pressure. The residue was recrystallized from ethyl acetate-hexane to obtain the title compound (2.36 g, 36.8%)) as colorless prism.

$^1$H-NMR (CDCl$_3$)δ:1.50–1.91(5H,m), 2.06–2.16(1H,m), 3.19–3.28(1H,m), 7.18–7.33(3H,m), 7.48–7.53(2H,m).

Example 1

Preparation of N-(1-benzyl-4-piperidinyl)-2-ethoxy-3-methyl-2-phenylbutanamide (the invention compound, Compound No. 1)

Under ice cooling, oxalyl chloride (15 ml) was added to a solution of 2-ethoxy-3-methyl-2-phenylbutanoic acid (Compound (7), 14 g) in anhydrous benzene (100 ml). To the resulting mixture, 1 ml of dimethylformamide was added, followed by stirring at room temperature for 4 hours. The excess oxalyl chloride was then removed under reduced pressure. To the residue, a solution of 4-amino-1-benzyl-piperidine (34.3 g) in benzene (150 ml) was added dropwise and the resulting mixture was stirred overnight at room temperature. To the reaction mixture, a 1N aqueous sodium hydroxide solution was added to make it basic, followed by extraction with ethyl acetate. The organic layer was washed with brine and dried over anhydrous sodium sulfate. The solvent was then removed under reduced pressure. The residue was purified by a silica gel column to obtain the invention compound (Compound No. 1, 23.0 g, 92.5%) as a colorless oil. The data of the compound are shown in Table 1.

Example 2

In a similar manner to Example 1, the invention compounds (Compounds Nos. 2 to 15, 17 to 23, 26 and 34) were prepared.

Example 3

Preparation of 1-benzyl-4-[(2-ethoxy-3-methyl-2-phenylbutanoyl)amino]piperidin-1-oxide (the invention compound, Compound No. 16)

To a dissolved solution of N-(1-benzyl-4-piperidinyl)-2-ethoxy-3-methyl-2-phenylbutanamide (invention compound, Compound No. 1) (400 mg, 1.01 mmole) in chloroform (20 ml) was added 70% m-chloroperbenzoic acid (271 mg, 1.1 mmole). The mixture was stirred at room temperature for 3 days. After the reaction was completed, the reaction mixture was washed with a saturated aqueous sodium bicarbonate solution. The organic layer was dried over anhydrous sodium sulfate. The solvent was then removed under reduced pressure. The residue was purified by a silica gel column to obtain the invention compound (Compound No. 16, 316 mg, 77.0%) were obtained as colorless solid.

Example 4

In a similar manner to Example 3, the invention compound (Compound No. 42) was prepared.

Example 5

Preparation of N-(1-benzyl-4-piperidinyl)-2-butoxy-3-methyl-2-phenylbutanamide (the invention compound, Compound No. 4)

To a solution of N-(1-benzyl-4-piperidinyl)-2-hydroxy-3-methyl-2-phenylbutanamide (20.0 g) in DMF (200 ml) was added sodium hydride (9.0 g). The resulting mixture was stirred at room temperature for one hour, followed by the dropwise addition of butyl iodide (8.3 ml) and a solution of tetra-n-butylammonium iodide (1.8 g) in DMF (30 ml) under ice cooling. Two hours later, butyl iodide (8.3 ml) and a solution of tetra-n-butylammonium iodide (1.8 g) in DMF (30 ml) were added dropwise again over 15 minutes under ice cooling, followed by stirring overnight at room temperature. The reaction mixture was poured into ice water (500 ml). The mixture was extracted with ethyl acetate (300 ml×2) to separate the organic layer. The organic layer so obtained was washed with water and dried over anhydrous sodium sulfate. The solvent was then removed under pressure. To the residue, 100 ml of ether and 100 ml of hexane were added. After the starting materials so precipitated were filtered off, the solvent was removed under reduced pressure. The residue was purified by a silica gel column to obtain the invention compound (Compound No. 4, 6.50 g, 28.2%) as a colorless oil.

Example 6

In a similar manner to Example 5, the invention compounds (Compounds Nos. 24, 31, 33, 35 to 41, 43 to 45, 47 to 49 and 50) were prepared.

Example 7

Preparation of N-(4-piperidinyl)-2-butoxy-3-methyl-2-phenylbutanamide (the invention compound, Compound No. 27)

To a solution of N-(1-benzyl-4-piperidinyl)-2-butoxy-3-methyl-2-phenylbutanamide (invention compound, Compound No. 4) (4.5 g, 10.6 mmole) in ethanol (60 ml) was added palladium hydroxide-carbon (1.2 g), followed by hydrogenation for 6 hours at room temperature. The catalyst was filtered off and the filtrate was removed under reduced pressure to obtain the invention compound (Compound No. 27, quantitative yield) as a colorless oil.

Example 8

Preparation of N-{1-(4-methoxybenzyl)-4-piperidinyl}-2-butoxy-3-methyl-2-phenylbutanamide (the invention compound, Compound No. 29)

N-(4-Piperidinyl)-2-butoxy-3-methyl-2-phenylbutanamide (invention compound, Compound No. 27) (4.5 g) was dissolved in dioxane (25 ml) and water (25 ml). To the resulting solution, potassium carbonate (0.7 g) and 4-methoxybenzyl chloride (0.8 g) were added, followed by stirring at room temperature for 2 days. To the reaction mixture, was added water (40 ml). The resulting mixture was extracted with an ethyl acetate. The extract was then dried over anhydrous sodium sulfate and the solvent was removed under reduced pressure. The residue was purified by a silica gel column to obtain the invention compound (Compound No. 29, 0.60 g, 26.4%) as a colorless oil.

Example 9

In a similar manner to Example 8, the invention compounds (Compounds Nos. 28, 30, 32 and 46) were prepared.

The chemical structure, melting point and NMR data of each of the compounds obtained in the above examples are shown in Tables 1 to 7.

TABLE 1

| Com. No. | R¹ | R² | R³ | R⁴ | n | Melting point (°C.) Hydrochloride | ¹H—NMR(Hydrochloride DMSO-d₆, δ) |
|---|---|---|---|---|---|---|---|
| 1 | phenyl | isopropyl | CH₂CH₃ | benzyl | 0 | 155–157 | 0.79(3H, d), 0.87(3H, d), 1.12(3H, t), 1.80–2.14(4H, m), 2.60–2.70(1H, m), 2.85–3.35(4H, m), 3.20(2H, q), 3.86(0.8H, br), 4.05(0.2H, br), 4.23(1.6H, d), 4.35(0.4H, d), 7.24–7.71(11H, m), 11.12(0.8H, br), 11.25(0.2H, br) |
| 2 | phenyl | isopropyl | CH₃ | benzyl | 0 | 142–145 | 0.80(3H, d), 0.90(3H, d), 1.80–2.10(4H, m), 2.60–2.70(1H, m), 2.90–3.30(4H, m), 3.03(3H, s), 3.87(0.8H, br), 4.08(0.2H, br), 4.23(1.6H, d), 4.35(0.4H, d), 7.24–7.80((11H, m), 11.12(0.8H, br), 11.26(0.2H, br) |
| 3 | phenyl | isopropyl | CH₂CH₃ | benzyl | 0 | 128–130 | 0.78–0.89(9H, m), 1.53(2H, q), 1.82–2.07(4H, m), 2.60–2.72(1H, m), 2.93–3.41(6H, m), 3.89(0.8H, br), 4.06(0.2H, br), 4.24(1.6H, d) 4.35(0.4H, d), 7.24–7.66(11H, m), 11.12(0.8H, br), 11.28(0.2H, br) |
| 4 | phenyl | isopropyl | CH₂CH₂CH₃ | benzyl | 0 | 97–99 | 0.78–0.88(9H, m), 1.29(2H, q), 1.46–1.54(2H, m), 1.82–2.08(4H, m), 2.61–2.69(1H, m), 2.93–3.40(6H, m), 3.89(0.8H, br), 4.07(0.2H, br), 4.24(1.6H, d), 4.35(0.4H, d), 7.25–7.66(11H, m), 11.13(0.8H, br), 11.30(0.2H, br) |
| 5 | phenyl | cyclopentyl | CH₃ | benzyl | 0 | 205–208 | 1.35–2.10(13H, m), 2.88(1H, t), 2.90–3.35(3H, m), 3.03(3H, s), 3.85(0.8H, br), 4.06(0.2H, br), 4.23(1.6H, d), 4.35(0.4H, d), 7.25–7.46(8H, m), 7.65(2H, s), 7.79(0.2H, d), 7.89(0.8H, d), 10.98(0.8H, br), 11.13(0.2H, br) |

TABLE 1-continued

| Com. No. | R¹ | R² | R³ | R⁴ | n | Melting point (° C.) Hydrochloride | ¹H—NMR(Hydrochloride DMSO-$d_6$, δ) |
|---|---|---|---|---|---|---|---|
| 6 | phenyl | cyclopentyl | CH$_2$CH$_3$ | benzyl(ethyl) | 0 | 153–156 | 1.10(3H, t), 1.27–2.08(13H, m), 2.86(1H, t), 2.90–3.37(3H, m), 3.85(0.8H, br), 4.04(0.2H, br), 4.23(1.6H, d), 4.36(0.4H, d), 7.24–7.70(11H, m), 11.13 (0.8H, br), 11.27(0.2H, br) |
| 7 | phenyl | cyclopentyl | CH$_2$CH$_2$CH$_3$ | benzyl(ethyl) | 0 | 104–106 | 0.82(3H, t), 1.28–2.12(15H, m), 2.87(1H, t), 2.90–3.35(5H, m), 3.86(0.8H, br), 4.04(0.2H, br), 4.23(1.6H, d), 4.35(0.4H, d), 7.24–7.65(11H, m), 11.07 (0.8H, br), 11.23(0.2H, br) |
| 8 | phenyl | cyclohexyl | CH$_3$ | benzyl(ethyl) | 0 | 175–177 | 0.76–2.26(15H, m), 3.00(3H, s), 3.01–3.03(2H, m), 3.20–3.40(2H, m), 3.80–3.90(0.8H, m), 4.02–4.10(0.2H, m), 4.22(1.6H, d), 4.34(0.4H, d), 7.24–7.85 (11H, m), 11.02(0.8H, br), 11.17(0.2H, br) |
| 9 | phenyl | cyclohexyl | CH$_2$CH$_3$ | benzyl(ethyl) | 0 | 174–176 | 0.70–0.95(3H, m), 1.11(3H, t), 1.21–2.26(12H, m), 2.90–3.05(2H, m), 3.16–3.20(2H, m), 3.22–3.39(2H, m), 3.80–3.90(0.8H, m), 4.02–4.10(0.2H, m), 4.23(1.6H, d), 4.36(0.4H, d), 7.23–7.62(11H, m), 10.88(0.8H, br), 11.05 (0.2H, br) |

TABLE 2

| Com. No. | R¹ | R² | R³ | R⁴ | n | Melting point (°C.) Hydrochloride | ¹H—NMR(Hydrochloride DMSO-$d_6$, δ) |
|---|---|---|---|---|---|---|---|
| 10 | phenyl | cyclohexyl | $CH_2CH_2CH_3$ | benzyl(ethyl) | 0 | 139–141 | 0.71–0.76(1H, m), 0.83(3H, t), 0.84–0.94(2H, m) 1.09–2.27(12H, m), 3.02–3.16(4H, m), 3.20–3.41(4H, m) 3.80–3.90(0.8H, m), 4.02–4.10(0.2H, m), 4.23(1.6H, d), 4.36(0.4H, d), 7.26–7.61(11H, m), 10.71(0.8H, br), 10.92 (0.2H, br) |
| 11 | phenyl | cyclopropyl | $CH_2CH_3$ | benzyl(ethyl) | 0 | 92–95 (Fumarate) | 0.24–0.29(1H, m), 0.53–0.62(3H, m), 1.14(3H, t), 1.42–1.70(5H, m), 2.08–2.17(2H, m) 2.73–2.82(2H, m), 3.25–3.42(2H, m), 3.52(2H, s), 3.50–3.68 (1H, m) 6.61(2H, s), 7.23–7.40(9H, m), 7.44–7.47(2H, m) (Fumarate) |
| 12 | phenyl | cyclopropyl | $CH_2CH_2CH_3$ | benzyl(ethyl) | 0 | 124–127 (Fumarate) | 0.24–0.30(1H, m), 0.50–0.64(3H, m), 0.87(3H, t), 1.43–1.77(7H, m), 2.02–2.27(2H, m), 2.75–2.86(2H, m), 3.22–3.33(2H, m), 3.59(2H, s), 3.52–3.70 (1H, m), 6.62(2H, s), 7.24–7.35(9H, m), 7.45(2H, d) (Fumarate) |
| 13 | phenyl | cyclobutyl | $CH_2CH_3$ | benzyl(ethyl) | 0 | 142–145 (Fumarate) | 1.11(3H, t), 1.48–2.04(9H, m), 2.15–2.26(3H, m), 2.77–2.88(2H, m), 3.12–3.29(3H, m), 3.58(2H, s), 3.63–3.79(1H, m), 6.61(2H, s), 7.24–7.40(10H, m), 7.39(1H, d)(Fumarate) |
| 14 | phenyl | cyclobutyl | $CH_2CH_2CH_3$ | benzyl(ethyl) | 0 | 123–126 (Fumarate) | 0.85(3H, t), 1.46–2.06(11H, m), 2.13–2.29(3H, m), 2.70–2.84(2H, m), 3.02–3.23(3H, m), 3.52(2H, s), 3.62–3.80(1H, m), 6.61(2H, s), 7.23–7.35(11H, m) (Fumarate) |

TABLE 2-continued

| Com. No. | R¹ | R² | R³ | R⁴ | n | Melting point (°C.) Hydrochloride | ¹H—NMR(Hydrochloride DMSO-d₆, δ) |
|---|---|---|---|---|---|---|---|
| 15 | phenyl | isopropyl | CH₂CH₃ | CH₃ | 0 | 60–62 (Fumarate) | 0.80(3H, d), 0.89(3H, d), 1.12(3H, t), 1.63–1.84(4H, m), 2.41(3H, s), 2.45–2.55(2H, m), 2.58–2.69(1H, m), 2.95–3.10(2H, m), 3.17–3.27(2H, m), 3.69–3.84(1H, m), 6.55(2H, s), 7.24–7.50(5H, m) (Fumarate) |
| 16 | phenyl | isopropyl | CH₂CH₃ | benzyl | 1 | 180–182 (Free base) | 0.79(3H, d), 0.89(3H, d), 1.11(3H, t), 1.58–1.69(2H, m), 2.20–2.30(2H, m), 2.60–2.67(1H, m), 3.05–3.15(2H, m), 3.15–3.25(2H, m), 3.30–3.45(2H, m), 3.75–3.90(1H, m), 4.48(2H, s), 7.24–7.60(11H, m) (Free) |
| 17 | phenyl | cyclohexyl | CH₂CH₂CH₂CH₃ | benzyl | 0 | 145–147 | 0.70–1.10(3H, m), 0.82(3H, t), 1.20–1.32(4H, m), 1.45–1.69(6H, m), 1.80–2.15(5H, m), 2.25(1H, t), 2.90–3.40(6H, m), 3.89(0.8H, br), 4.06(0.2H, br), 4.23(1.6H, d), 4.36(0.4H, d), 7.24–7.50(9H, m), 7.65(2H, d), 11.11(0.8H, br), 11.30(0.2H, br) |

TABLE 3

| Com. No. | R¹ | R² | R³ | R⁴ | n | Melting point (° C.) Hydrochloride | ¹H—NMR(Hydrochloride DMSO-d₆, δ) |
|---|---|---|---|---|---|---|---|
| 18 | phenyl | cyclohexyl | CH₂CH₃ | CH₃ | 0 | 178–181 (3/2 Fumarate) | 0.74–0.96(5H, m), 1.11(3H, t), 1.18–1.26(2H, m), 1.55–1.95(8H, m), 2.20–2.26(1H, m), 2.46(3H, s), 2.57–2.62(2H, m), 3.06–3.16(2H, m), 3.17–3.20 (2H, m), 3.90(1H, m), 6.57(3H, s), 7.24–7.40(5H, m), 7.48(1H, d) (Fumarate) |
| 19 | phenyl | cyclohexyl | CH₂CH₂OH | benzyl | 0 | 100–102 (Fumarate) | 0.84–1.35(6H, m), 1.50–1.84(7H, m), 2.01–2.22(4H, m), 2.81–2.92(2H, m), 2.98–3.05(2H, m), 3.43–3.58(2H, m), 3.56(2H, s), 3.72(1H, br), 6.62(2H, s), 7.23–7.36(8H, m), 7.47(2H, d), 8.10(1H, d)(Fumarate) |
| 20 | phenyl | cyclohexyl | CH₂CH₂N(CH₃)₂ | benzyl | 0 | 161–162 (2 Fumarate) | 0.74–1.30(5H, m), 1.42(1H, d), 1.52–1.80(7H, m), 1.98(1H, d), 2.11–2.22 (3H, m), 2.43(6H, s), 2.67–2.90(4H, m), 3.07–3.22(2H, m), 3.56(2H, s), 3.73 (1H, br), 6.58(4H, s), 7.23–7.46(10H, m), 8.08(1H, d) (Fumarate) |
| 21 | phenyl | cyclohexyl | CH₂CH₂N(CH₂CH₃)₂ | benzyl | 0 | 170–171 (3/2 Fumarate) | 0.75–1.42(6H, m), 1.04(6H, t), 1.50–1.82(7H, m), 1.94–2.20(4H, m), 2.68–2.90(4H, m), 2.71(4H, q), 3.07–3.17(2H, m), 3.53(2H, m), 3.72(1H, br), 6.58 (3H, s), 7.23–7.35(8H, m), 7.42(2H, d), 8.00(1H, m), 8.00(1H, d) (Fumarate) |
| 22 | phenyl | cyclohexyl | CH₂CH₂CH₂-morpholine | benzyl | 0 | 162–163 (3/2 Fumarate) | 0.74–1.28(5H, m), 1.43–1.82(8H, m), 1.94(1H, br), 2.14–2.24(3H, m), 2.37–2.56(6H, m), 2.78–2.87(2H, m), 3.09–3.22(2H, m), 3.52–3.65(4H, m), 3.57 (2H, s), 3.73(1H, br), 6.61(3H, s)(3H, s), 7.24–7.39(8H, m), 7.42(2H, d), 7.47 (1H, d)(Fumarate) |

TABLE 3-continued

| Com. No. | R¹ | R² | R³ | R⁴ | n | Melting point (° C.) Hydrochloride | ¹H—NMR(Hydrochloride DMSO-d₆, δ) |
|---|---|---|---|---|---|---|---|
| 23 | phenyl | cyclopentyl | (CH₂)₂CH₃ | benzyl | 0 | 97–99 | 0.82(3H, t), 1.20–2.17(16H, m), 2.75–3.40(7H, m), 3.86(0.8H, br), 4.07 (0.2H, br), 4.23(1.6H, d), 4.24(0.4H, d), 7.24–7.64(11H, m), 10.90(0.8H, br), 11.05(0.2H, br) |
| 24 | phenyl | isobutyl | (CH₂)₄CH₃ | benzyl | 0 | 101–103 | 0.78–0.88(9H, m), 1.22–1.26(4H, m), 1.50–1.55(2H, m), 1.75–2.10(4H, m), 2.65–2.70(1H, m), 2.95–3.35(6H, m), 3.88(0.8H, br), 4.10(0.2H, br), 4.23 (1.6H, d), 4.34(0.4H, d), 7.24–7.67(11H, m), 10.87(0.8H, br), 11.08(0.2H, br) |
| 25 | phenyl | isobutyl | (CH₂)₅CH₃ | benzyl | 0 | 100–102 | 0.78–0.88(9H, m), 1.18–1.30(6H, m), 1.45–1.57(2H, m), 1.82–2.12(4H, m), 2.60–2.70(1H, m), 2.90–3.30(6H, m), 3.90(0.8H, br), 4.08(0.2H, br), 4.23 (1.6H, d), 4.35(0.4H, d), 7.20–7.65(11H, m), 11.01(0.8H, br), 11.15(0.2H, br) |

TABLE 4-continued

| Com. No. | R¹ | R² | R³ | R⁴ | n | Melting point (°C.) Hydrochloride | ¹H—NMR(Hydrochloride DMSO-d₆, δ) |
|---|---|---|---|---|---|---|---|
| 31 | phenyl | 1-methyl-4-piperidinyl | $(CH_2)_2CH_3$ | benzyl | 0 | 134–136 (Fumarate) | 0.83(3H, t), 1.25–1.35(3H, m), 1.45–1.77(8H, m), 1.98(1H, d), 2.08–2.15 (2H, m), 2.42–2.80(5H, m), 2.49(3H, m), 3.24–3.90(4H, m), 3.49(2H, s), 3.70 (1H, br), 6.54(4H, s), 7.22–7.38(11H, m)(Fumarate) |
| 32 | phenyl | isobutyl | $(CH_2)_3CH_3$ | 4-nitrobenzyl | 0 | Oil (Free base) | 0.78–1.20(9H, m), 1.20–3.48(15H, m), 3.60(2H, s), 3.88(1H, br)6.74 (1H, d), 7.20–7.60(7H, m), 8.17(2H, d)(CDCl₃)(free) |
| 33 | 2-pyridyl | isobutyl | $(CH_2)_3CH_3$ | benzyl | 0 | Amorphous (Fumarate) | 0.79–0.87(9H, m), 1.24–1.31(2H, m), 1.41–1.59(4H, m), 1.70–1.85(2H, m), 2.18–2.23(2H, m), 2.72 2.77(3H, m), 3.08–3.18(2H, m), 3.53(2H, s), 3.74– 3.76(1H, m), 6.61(2H, s), 7.23–7.42(7H, m), 7.78–7.83(1H, m), 8.06–8.08 (1H, d), 8.54–8.56(1H, d)(Fumarate) |

TABLE 5

| Com. No. | R¹ | R² | R³ | R⁴ | n | Melting point (°C) Hydrochloride | ¹H—NMR(Hydrochloride DMSO-d₆, δ) |
|---|---|---|---|---|---|---|---|
| 34 | 4-OMe-phenyl | isopropyl | CH₂CH₂OH | benzyl(CH₂) | 0 | 180–181 (Fumarate) | 0.79(3H, d), 0.94(3H, d), 1.50–1.60(2H, m), 1.72–1.82(2H, m), 2.13–2.21 (2H, m), 2.45–2.53(1H, m), 2.80–2.85(2H, m), 3.02–3.09(2H, m), 3.45–3.59 (2H, m), 3.55(2H, s), 3.70–3.74(1H, m), 6.61(2H, s), 7.24–7.35(8H, m), 7.48 (2H, d), 8.08(1H, d)(Fumarate) |
| 35 | phenyl | isopropyl | (CH₂)₂CH(CH₃)₂ | benzyl(CH₂) | 0 | Oil (Free base) | 0.70–1.15(12H, m), 1.25–3.45(14H, m), 3.50(2H, s), 3.87(1H, br), 6.75(1H, d), 7.20–7.60(10H, m)(CDCl₃)(free) |
| 36 | 3-OMe-phenyl | cyclopentyl | (CH₂)₃CH₃ | benzyl(CH₂) | 0 | Oil (Free base) | 0.75–1.07(3H, m), 1.10–3.45(23H, m), 3.48(2H, s), 3.78(3H, s), 3.82(1H, br), 6.70–7.50(10H, m)(CDCl₃)(free) |
| 37 | 4-OMe-phenyl | isopropyl | (CH₂)₂CH₃ | benzyl(CH₂) | 0 | Oil (Free base) | 0.90(3H, t), 0.92(3H, d), 0.97(3H, d), 1.45–1.56(4H, m), 1.81–1.96(2H, m), 2.11–2.19(2H, m), 2.62–2.79(3H, m), 3.01–3.20(2H, m), 3.49(2H, s), 3.80–3.87(4H, m), 6.76(1H, d), 6.83–6.87(2H, m), 7.23–7.37(7H, m)(CDCl₃) (free) |
| 38 | 4-OMe-phenyl | isopropyl | (CH₂)₃CH₃ | benzyl(CH₂) | 0 | Oil (Free base) | 0.89(3H, t), 0.94(3H, d), 1.00(3H, d), 1.30–1.55(6H, m), 1.86–1.96(2H, m), 2.11–2.18(2H, m), 2.63–2.79(3H, m), 3.06–3.24(2H, m), 3.49(2H, s), 3.79–3.87(4H, m), 6.75(1H, d), 6.82–6.86(2H, m), 7.23–7.36(7H, m)(CDCl₃) (free) |
| 39 | 4-OMe-phenyl | isopropyl | (CH₂)₂CH(CH₃)₂ | benzyl(CH₂) | 0 | Oil (Free base) | 0.86(3H, d), 0.87(3H, d), 0.95(3H, d), 1.00(3H, d), 1.37–1.53(4H, m), 1.62–1.69(1H, m), 1.87–1.96(2H, m), 2.13–2.21(2H, m), 2.64–2.83(3H, m), 3.08–3.14(1H, m), 3.20–3.27(1H, m), 3.49(2H, s), 3.84–3.86(4H, m), 6.77(1H, d), 6.83–6.87(2H, m), 7.23–7.36(7H, m)(CDCl₃)(free) |
| 40 | 4-OMe-phenyl | cyclopentyl | (CH₂)₃—Ph | benzyl(CH₂) | 0 | Oil (Free base) | 1.39–1.91(14H, m), 2.14–2.19(2H, m), 2.61–2.95(5H, m), 3.13–3.32(2H, m), 3.48(2H, s), 3.79–3.85(4H, m), 6.81–6.86(3H, m), 7.12–7.35(12H, m) (CDCl₃)(free) |

TABLE 6

| Com. No. | R¹ | R² | R³ | R⁴ | n | Melting point (° C.) Hydrochloride (Free base) | ¹H—NMR(Hydrochloride DMSO-d₆, δ) |
|---|---|---|---|---|---|---|---|
| 41 |  3-Cl-C₆H₄ | cyclopentyl | CH₂Ph | 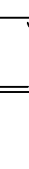 CH₂CH₂Ph | 0 | Oil (Free base) | 1.39–1.58(6H, m), 1.70–1.79(2H, m), 1.82–1.94(4H, m), 2.10–2.18(2H, m), 2.68–2.70(2H, m), 2.94–3.02(1H, m), 3.44(2H, s), 3.78–3.85(4H, m), 4.20 (1H, d), 4.35(1H, d), 6.84–6.89(3H, m), 7.21–7.45(12H, m)(CDCl₃)(free) |
| 42 | phenyl | isobutyl | (CH₂)₃CH₃ | CH₂CH₂Ph | 1 | Oil (Free base) | 0.78–1.10(9H, m), 1.15–3.45(16H, m), 3.80(1H, br), 4.45(2H, s), 6.88(1H, d), 7.20–7.65(10H, m)(CDCl₃)(free) |
| 43 | 3-Me-C₆H₄ | cyclopentyl | (CH₂)₃CH₃ | CH₂CH₂Ph | 0 | Oil (Free base) | 0.75–1.08(3H, m), 1.10–3.40(23H, m), 3.50(2H, s), 3.82(1H, br), 6.75(1H, d), 7.15–7.53(9H, m)(CDCl₃)(free) |
| 44 | 3-OMe-C₆H₄ | isobutyl | (CH₂)₃CH₃ | CH₂CH₂Ph | 0 | Oil (Free base) | 0.70–1.12(9H, m), 1.17–3.38(15H, m), 2.32(3H, s), 3.50(2H, s), 3.85(1H, br), 6.72(1H, d), 7.00–7.43(9H, m)(CDCl₃)(free) |

TABLE 6-continued

| Com. No. | R¹ | R² | R³ | R⁴ | n | Melting point (°C.) Hydrochloride | ¹H—NMR(Hydrochloride DMSO-$d_6$, δ) |
|---|---|---|---|---|---|---|---|
| 45 | 3-OMe-phenyl | cyclopentyl | (CH$_2$)$_3$CH=CH$_2$ | benzyl | 0 | Oil (free base) | 1.30–4.16(24H, m), 3.50(2H, s), 3.83(3H, s), 4.85–5.18(2H, m), 5.48–6.06 (1H, m), 6.68–7.45(10H, m)(CDCl$_3$)(free) |
| 46 | phenyl | isobutyl | (CH$_2$)$_3$CH$_3$ | 3-pyridylethyl | 0 | Oil (Free base) | 0.75–3.40(24H, m), 3.50(2H, s), 3.53–4.15(1H, m), 6.74(1H, d), 7.18–7.82 (8H, m), 8.42–8.64(2H, m)(CDCl$_3$)(free) |
| 47 | phenyl | isobutyl | CH$_2$CH$_2$N(CH$_2$CH$_3$)$_2$ | benzyl | 0 | Amorphous (Fumarate) | 0.79(3H, d), 0.92(3H, d), 1.06(6H, t), 1.52–1.83(4H, m), 2.12–2.18(2H, m), 2.45–2.59(1H, m), 2.70–2.92(8H, m), 3.12–3.18(2H, m), 3.55(2H, d), 3.73 (1H, br), 6.59(4H, s), 7.23–7.45(10H, m), 7.97(1H, d)(Fumarate) |

TABLE 7

| Com. No. | R¹ | R² | R³ | R⁴ | n | Melting point (°C.) Hydrochloride | ¹H—NMR(Hydrochloride DMSO-d₆, δ) |
|---|---|---|---|---|---|---|---|
| 48 | 3-Cl-C₆H₄ | cyclohexyl | (CH₂)₃CH(CH₃)₂ | CH₂-C₆H₅ | 0 | Oil (Free base) | 0.85–2.23(28H, m), 2.75–2.83(2H, m), 2.98–3.04(1H, m), 3.11–3.18(1H, m), 3.49(2H, s), 3.78–3.88(4H, m), 6.76(1H, m), 6.81–6.89(2H, d), 7.18–7.35 (7H, m)(CDCl₃)(free) |
| 49 | 3-OMe-C₆H₄ | cyclopentyl | (CH₂)₃—Ph | CH₂-C₆H₅ | 0 | Oil (free base) | 1.40–1.88(14H, m), 2.14–2.17(2H, m), 2.62–2.95(5H, m), 3.19–3.25(1H, m), 3.30–3.36(1H, m), 3.48(2H, s), 3.78–3.83(4H, m), 6.79–6.82(2H, m), 6.98–7.02(2H, m), 7.13–7.31(11H, m), (CDCl₃)(free) |
| 50 | 3-CH₃-C₆H₄ | cyclopentyl | (CH₂)₃—Ph | CH₂-C₆H₅ | 0 | Oil (Free base) | 1.34–1.92(14H, m), 2.11–2.19(2H, m), 2.63–2.88(5H, m), 3.16–3.23(1H, m), 3.29–3.35(1H, m), 3.48(2H, s), 3.77–3.87(1H, d), 6.73(1H, d), 7.13–7.45 (14H, m)(CDCl₃)(free) |

Test 1

Action against acetylcholine-induced bladder contraction

Testing method

SD male rats weighing 230 to 390 g were each fixed on its back under intraperitoneal anesthesia with 500 mg/kg of urethane and 50 mg/kg of α-chloralose. Then, its bladder was exposed by midline abdominal incision. Into the top part of the bladder, a polyethylene tube filled with physiological saline was inserted and intracystic pressure was measured. Into the femoral vein, a venous cannula for administration of a drug was inserted, through which 10 μg/kg of acetylcholine were administered to induce bladder contraction. Then, acetylcholine was administered at intervals of 10 minutes. After the bladder contraction by acetylcholine became stable, the stomach was subjected to midline incision and the test compound was intraduodenally administered using an injection needle. For 120 minutes after that, the action of the compound against bladder contraction was observed.

The bladder contraction was measured as a difference of intracystic pressure before and after the administration of acetylcholine. In addition, the bladder contraction before the administration of a test compound was designated as a pre-administration value and based on the contraction after the administration of the test compound compared with the pre-administration value, a 50% inhibitory dose ($ID_{50}$) of the test compound was calculated. The results are shown in Table 8.

Test 2

Action against carbachol-induced hypersialosis Testing method

A test compound was orally administered to each of SD male rats weighing 100 to 150 g. Thirty minutes later, 0.1 mg/kg of carbachol was intraperitoneally administered. Immediately after the administration of carbachol, the rat was fixed by hands under non-anesthesia and under this condition, the saliva was wiped off with a cotton ball for 10 minutes. The weight of the saliva so obtained was measured. With the salivation amount of a control to which only an excipient was administered as 100%, the dose ($ID_{50}$) inhibiting 50% of the salivation was calculated. The results are shown in Table 8.

The priority Japanese Patent Application No. 9-300352 filed on Oct. 31, 1997, is incorporated herein be reverence in its entirety.

We claim:

1. An arylacetic amide derivative represented by the following formula (1):

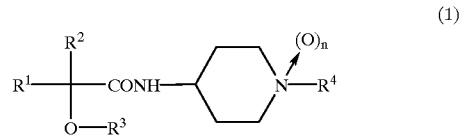

wherein $R^1$ represents a phenyl, naphthyl, thienyl, furanyl, imidazolyl, pyridyl, pyrazyl, pyrimidyl, pyridazyl, quinolyl, isoquinolyl, quinazolyl, quinoxalyl or cinnolyl group which may be substituted with one to five substituents selected from the group consisting of a halogen atom and halogeno $C_{1-6}$ alkyl), $C_{1-6}$ alkyl, $C_{1-6}$ alkoxy, amino, benzyloxy, cyano, benzoyl, $C_{1-6}$ alkanoyl, carbamoyl, carboxy, carboxy ($C_{1-6}$ alkyl), $C_{1-6}$ alkanoyloxy, nitro and sulfonamide groups, $R^2$ and $R^3$ each independently represents a $C_{1-8}$ linear, branched, cyclic or cyclic-linear alkyl, $C_{2-6}$ alkenyl, phenyl ($C_{1-6}$ alkyl), nitrogen-containing saturated heterocyclic or heteroaromatic-($C_{1-6}$ alkyl) group which may be substituted with a hydroxy group, amino group or substituted amino group, $R^4$ represents a phenyl, naphthyl, thienyl, furanyl, imidazolyl, pyridyl, pyrazyl, pyrimidyl, pyridazyl, quinolyl, isoquinolyl, quinazolyl, quinoxalyl, cinnolyl, phenyl ($C_{1-6}$ alkyl), or heteroaromatic-($C_{1-6}$ alkyl) group which may be substituted with one to five substituents selected from the group consisting of a halogen atom and halogeno ($C_{1-6}$ alkyl), $C_{1-6}$ alkyl, $C_{1-6}$ alkoxy, amino, benzyloxy, cyano, benzoyl, $C_{1-6}$ alkanoyl, carbamoyl, carboxy, carboxy ($C_{1-6}$ alkyl), $C_{1-6}$ alkanoyloxy, nitro and sulfonamide groups, and n stands for 0 or 1; or salt thereof.

2. A pharmaceutical which comprises as an effective ingredient an arylacetic amide derivative or salt thereof as claimed in claim 1.

3. A pharmaceutical according to claim 2, which is a preventive or remedy for urinary disorders.

TABLE 8

| | <Test results> | | | |
|---|---|---|---|---|
| Comp'd No. | Bladder contraction inhibitory action $ID_{50}$ (mg/kg) | Salivation inhibitory action $ID_{50}$ (mg/kg) | Salivation inhibitory action Bladder contraction inhibitory action | Selectivity |
| 3 | 9.4 | 33.9 | 3.6 | 4.0 |
| 4 | 9.8 | 56.6 | 5.8 | 6.2 |
| 12 | 10.0 | 22.5 | 2.3 | 2.4 |
| Oxybutynin hydrochloride | 3.4 | 3.5 | 1.0 | 1.1 |
| Propiverine hydrochloride | 9.9 | 9.2 | 0.9 | 1.0 |

From the above results, it has been found that the invention compound exhibited superior selectivity to bladder to oxybutynin hydrochloride or propiverine hydrochloride, which is a standard drug, and is useful as a preventive or remedy for urinary disorders such as pollakiuria or urinary incontinence in the diseases caused by nervous pollakiuria, neurogenic bladder, nocturnal enuresis, unstable bladder or chronic cystitis.

4. A pharmaceutical composition which comprises an arylacetic amide derivative or salt thereof as claimed in claim 1 and a pharmaceutically acceptable carrier.

5. A method of treating urinary disorders, which comprises administering an arylacetic amide derivative or salt thereof as claimed in claim 1.

* * * * *

UNITED STATES PATENT AND TRADEMARK OFFICE
CERTIFICATE OF CORRECTION

PATENT NO. : 6,060,485
DATED : May 9, 2000
INVENTOR(S) : Terumitsu Kaihoh et al.

It is certified that error appears in the above-identified patent and that said Letters Patent is hereby corrected as shown below:

<u>Column 38,</u>
Line 19, "$C_{1-6}$ alkyl)," should read -- ($C_{1-6}$ alkyl), --.

Signed and Sealed this

Second Day of November, 2004

JON W. DUDAS
*Director of the United States Patent and Trademark Office*